(12) United States Patent
Filtchev

(10) Patent No.: US 9,888,986 B2
(45) Date of Patent: Feb. 13, 2018

(54) SEMI-ADJUSTABLE, ARCON-TYPE ARTICULATOR

(71) Applicant: F ARTICULATOR DENT EOOD, Sofia (BG)

(72) Inventor: Andon Dimitrov Filtchev, Sofia (BG)

(73) Assignee: F ARTICULATOR DENT EOOD, Sofia (BG)

(*) Notice: Subject to any disclaimer, the term of this patent is extended or adjusted under 35 U.S.C. 154(b) by 0 days.

(21) Appl. No.: 15/107,731

(22) PCT Filed: Nov. 18, 2014

(86) PCT No.: PCT/BG2014/000041
§ 371 (c)(1),
(2) Date: Jun. 23, 2016

(87) PCT Pub. No.: WO2016/061644
PCT Pub. Date: Apr. 28, 2016

(65) Prior Publication Data
US 2016/0324603 A1  Nov. 10, 2016

(30) Foreign Application Priority Data
Oct. 22, 2014  (BG) ........................................ 111845

(51) Int. Cl.
*A61C 11/02* (2006.01)
*A61C 11/00* (2006.01)
(Continued)

(52) U.S. Cl.
CPC .......... *A61C 11/022* (2013.01); *A61C 11/003* (2013.01); *A61C 11/06* (2013.01); *A61C 11/087* (2013.01)

(58) Field of Classification Search
CPC ..... A61C 11/022; A61C 11/003; A61C 11/06; A61C 11/087
See application file for complete search history.

(56) References Cited

U.S. PATENT DOCUMENTS 2,765,533 A * 10/1956 McMorris ............. A61C 11/02
433/60
4,391,589 A *  7/1983 Monfredo ............. A61C 11/02
433/55
(Continued)

FOREIGN PATENT DOCUMENTS

CN  201029947 Y  3/2008
FR  1075074 A  10/1954
(Continued)

OTHER PUBLICATIONS

International Search Report for international Application No. PCT/BG2014/000041 dated Jun. 11, 2015.

*Primary Examiner* — Cris L Rodriguez
*Assistant Examiner* — Hao D Mai
(74) *Attorney, Agent, or Firm* — Brown & Michaels, PC

(57) ABSTRACT

Articulator—semiadjustable, arcon with lower and upper parts that could be detached from one another or interconnected, with two mechanical joints. An upper horizontal shoulder (5) is fixed to an elevator (4), said elevator (4) is connected to an upper vertical body (11) and can move vertically to adjust the vertical position. A lower vertical body (10) is fixed to the base (1) and holds an axis with two joint heads (14). The upper vertical body (11) is pivotably connected to the lower vertical body (10) through the two joint heads (14), the distance between the joint heads can vary due to an elastic element (18), thus reproducing the lateral shift. The articulation between the vertical bodies (11 and 10) can be locked and unlocked via an elbow shaped piece (13). The articulator lower part has an incisive platform (8) with a position angle that could be adapted.

3 Claims, 7 Drawing Sheets

(51) Int. Cl.
*A61C 11/06* (2006.01)
*A61C 11/08* (2006.01)

(56) References Cited

U.S. PATENT DOCUMENTS

| | | | | |
|---|---|---|---|---|
| 5,266,029 A * | 11/1993 | Feher | ............... | A61C 11/022 |
| | | | | 433/61 |
| 5,385,470 A * | 1/1995 | Polz | ............... | A61C 11/022 |
| | | | | 433/57 |
| 5,716,209 A * | 2/1998 | Faierstain | ............... | A61C 11/082 |
| | | | | 433/60 |
| 6,299,442 B1 * | 10/2001 | Shiao | ............... | A61C 11/022 |
| | | | | 433/64 |
| 6,386,868 B1 * | 5/2002 | Fujita | ............... | A61C 11/08 |
| | | | | 433/55 |
| 6,558,161 B2 * | 5/2003 | Nagata | ............... | A61C 11/022 |
| | | | | 433/57 |

FOREIGN PATENT DOCUMENTS

| | | | |
|---|---|---|---|
| FR | 2498924 | A2 | 8/1982 |
| NL | 8006043 | A | 6/1982 |
| WO | 2014146179 | A1 | 9/2014 |

* cited by examiner

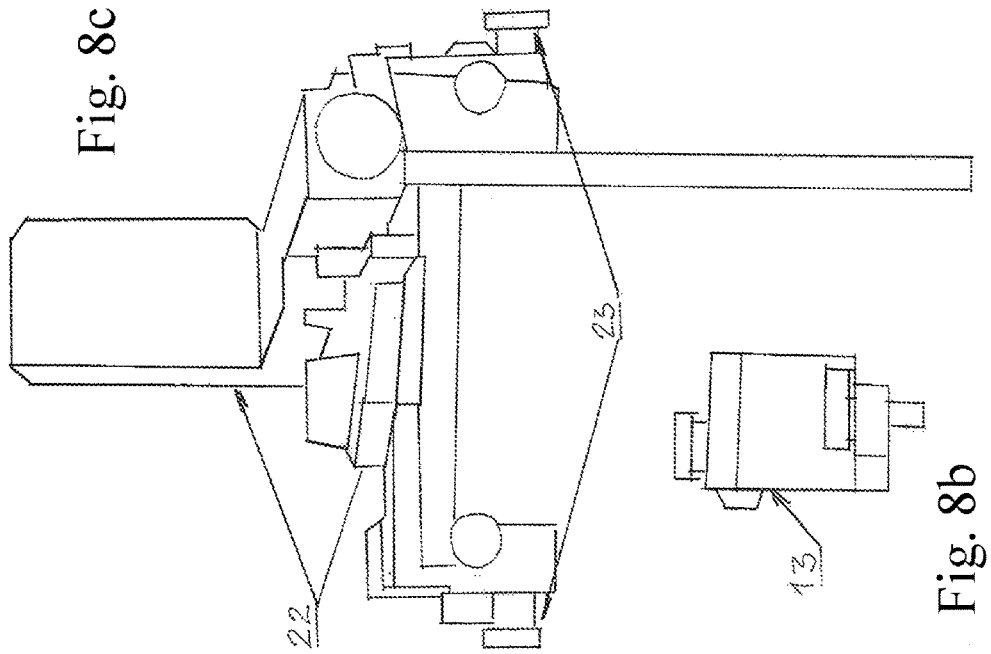
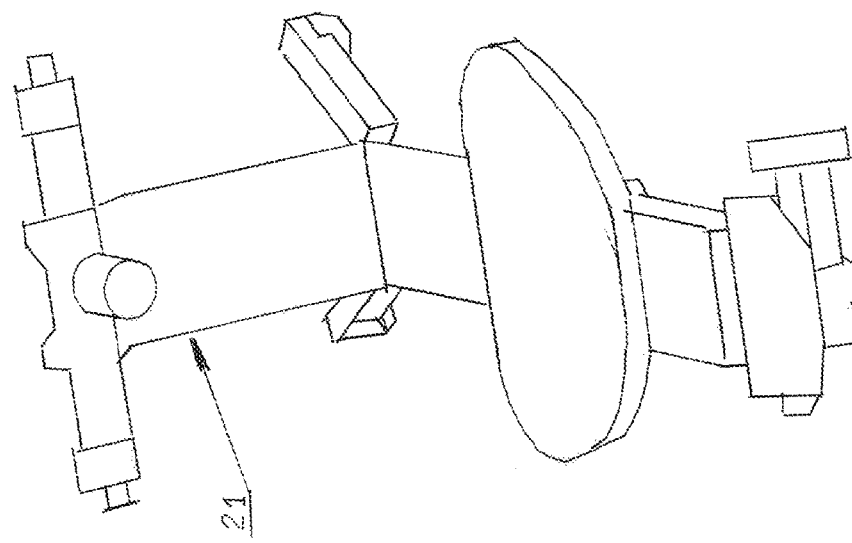

SEMI-ADJUSTABLE, ARCON-TYPE ARTICULATOR

FIELD OF THE INVENTION

The invention pertains to a semi-adjustable, arcon-type articulator for dental medicine and dental technique, and serves for fixing and analyzing working models, preparation of prosthetic constructions, and reproduction of lower mandible positions and movements versus the upper maxillar outside a patient's oral cavity.

BACKGROUND OF THE INVENTION

We have information about "Articulator" that is described in DE 195 30 157 A1; A61C11/02, containing the upper plate for fixing the maxillary working model and lower plate for fixing the mandibular working model. The articulator is partially adjustable (Semiadjustable—SA) and could reproduce in terms of individual values not all but part of the basic lower mandible movements: opening and closing, protrusion, retrusion, laterotrusion, and mediotrusion—progressive lateral shifting.

The joint cavity in the mechanical joint is in the shape of rounded groove, which is located at the interior of the semi-circular body. Joint head of spherical shape fits in the joint cavity. At the front the articulator contains incisive pin and incisive platform with shaped up inclinations of incisive lead, on the left and on the right, versus the middle line. This articulator has the following shortcomings: both mechanical joints are interconnected at fixed distance; they are more massive and volumetric; in-between the lower and upper working plate there is greater distance thus hindering the connection of the working models to them; there is no fixing mechanical device that is supposed to maintain at the rear the intra-parallel upper and lower plate of the articulator; the incisive platform cannot rotate.

We have information about articulators (Semiadjustable) that from "nonarcon" turned into "arcon"—articulator condition. In the mentioned bibliography source N 2 is presented as Dentatus ARL (previous model—Nonarcon) was transformed into Dentatus ARA (new model—Arcon) and Hanau 96 H 20 (previous model—Nonarcon) was transformed into Hanau, H2 (new model—Arcon). In the cases of the two abovementioned articulators the mechanical joints in the new model are the same just like in the previous model, but with exchanged locations of the joint cavity and the joint head. The mechanical joints of the articulators arcon—Dentatus ARA and of Hanau, H2 correspond to the human temporomandibular joint: the joint head is located at the lower mandible, at articulator's lower shoulder correspondingly, and the joint cavity is at the upper mandible, at articulator's upper shoulder correspondingly, while in the case of nonarcon—the articulators Dentatus ARL and Hanau 96 H 20 is the opposite of the human temporomandibular joint: the joint head is at articulator's upper shoulder, and the joint cavity is at the lower shoulder and when operating them minimum inaccuracy is allowed. Thus their mechanical joints were reconstructed, in order to obtain the functional capacities of the arcon articulators.

There are various virtual articulators that are copies of the actually existing articulators with partial adjustability (Semiadjustable). They are applied in the computer programmes for preparing the dental prosthetic constructions according to the CAD/CAM technology. The dental prostheses are being constructed and modeled in the CAD device, via virtual juxtaposition between the virtual working models included in the virtual articulator. After completing their design they are sent to the CAM machine for milling them out of a ceramic or metal block.

We are searching for manners and means for: improving the capacities of this articulator class—"semiadjustable, arcon"; cutting down the materials consumption; facilitating the operations performed with them; improving the accuracy and precision when preparing dental prostheses.

SUMMARY OF THE INVENTION

The task of the invention is to create a semi-adjustable, arcon-type articulator, as its construction will include new details—articulator parts with which to improve its capacities.

The offered semi-adjustable, arcon-type articulator is designed of two parts: lower and upper. On the base of the lower part, a magnetically connected working plate is located upwards, to which a mandibular working model is fixed. At a front of the base, an incisive platform is assembled on the base. At a rear of the base, the base is connected to a lower vertical body, to which a horizontal axis of variable length is connected. Joint heads are shaped up at both ends of the horizontal axis. To each joint head a body of a joint cavity is adapted that is connected to the articulator's upper part. The joint head and the body of the joint cavity could be movably or immovably connected, with the opportunity to separate the upper from the lower part of the articulator and to be fixed once again. Both bodies of the joint cavities in the upper part are connected to a plank that, in the middle, is connected to the upper vertical body. An elevator is assembled at a front of the upper vertical body. The upper vertical body at the front of the upper vertical body is connected to an upper horizontal shoulder, under which the magnetically connected working plate is located. The lower vertical body and the upper vertical body at a rear of the lower vertical body and a rear of the upper vertical body could be immovably blocked with an elbow. At a front of the upper horizontal shoulder, an incisive pin is assembled that leans on the incisive platform.

BRIEF DESCRIPTION OF THE DRAWINGS

The invention "Articulator semiadjustable, arcon" is described at the attached figures, where:

FIG. 8a shows a lower part of the articulator depicted in FIG. 1.

FIG. 8b shows an upper part of the articulator depicted in FIG. 1.

FIG. 8c shows an elbow of the articulator depicted in FIG. 1.

Figure 1:
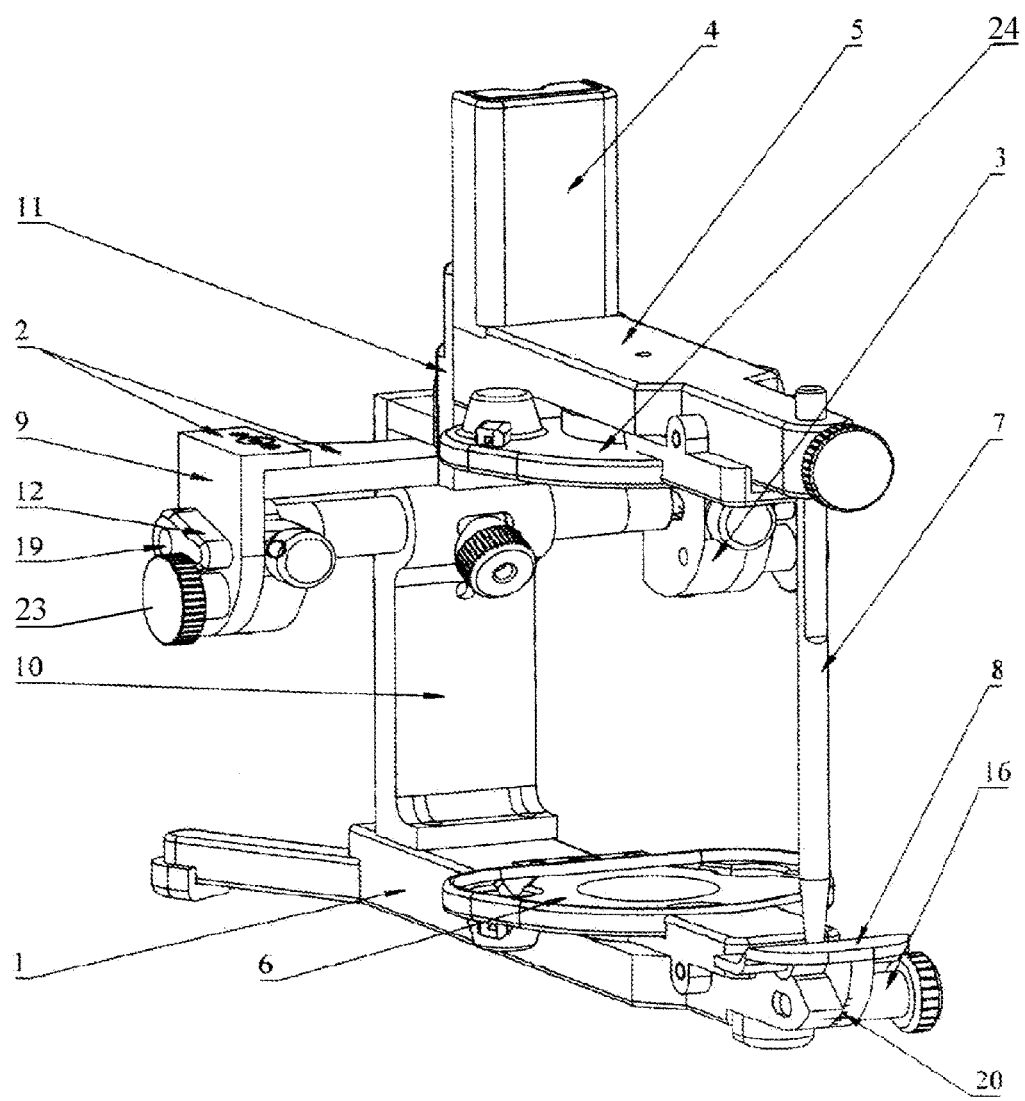
FIG. 1 contains drawing of the articulator, of frontal and lateral view, with presented digital numbers of the details 1,2,3,4,5,6,7,8,9,10,11,12,16,20.
Figure 2:
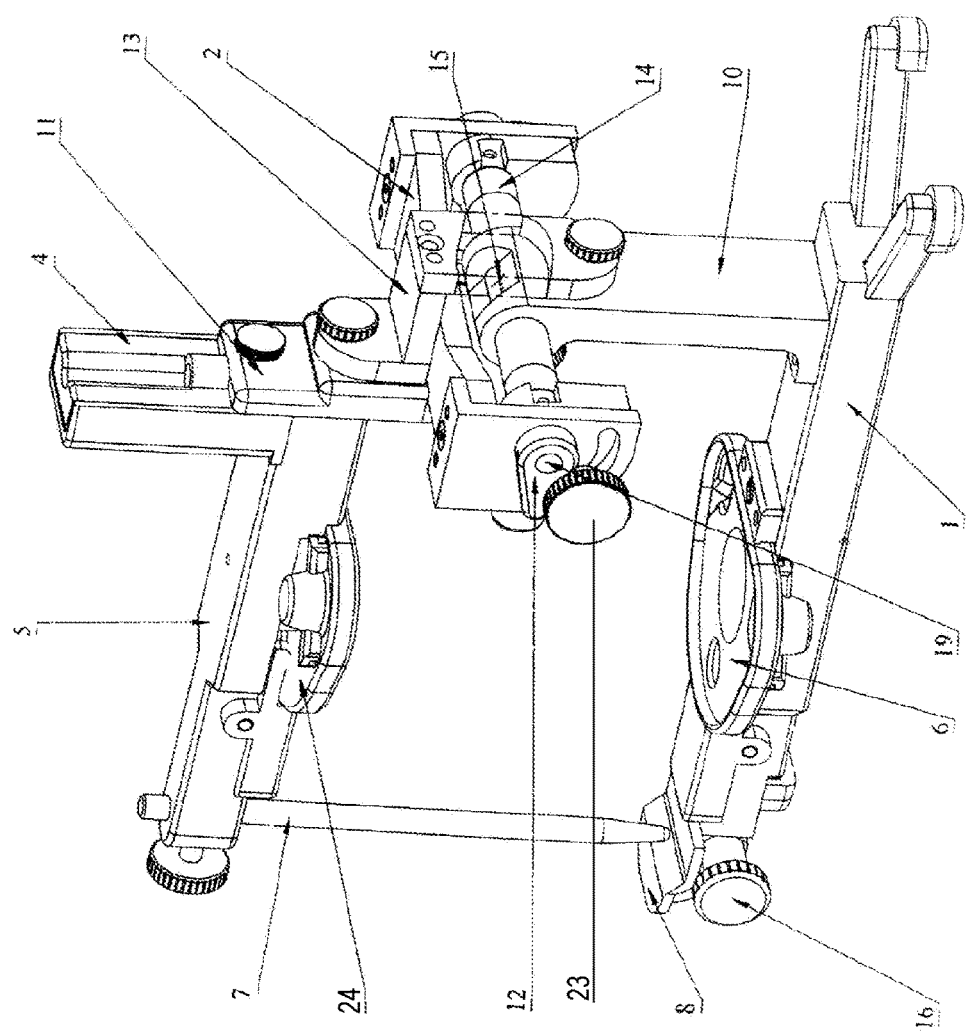
FIG. 2 presents the articulator of rear and lateral view, with presented digital numbers of the details 1,2,4,5,6,7,8, 10,11,12,13,14,15,16,19,20.
Figure 3:
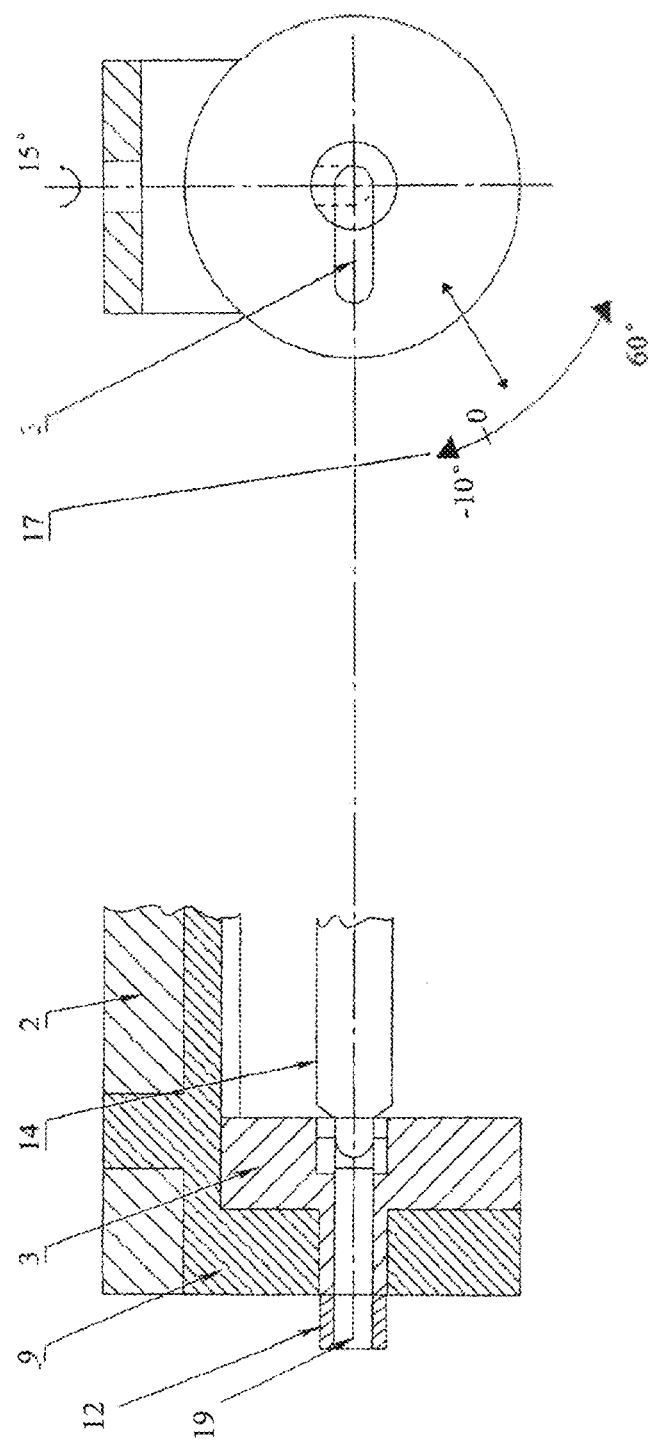
FIG. 3 presents a section of articulator's mechanical joint, with the following numbered details 2,3,9,12,14,17,19.
Figure 4:
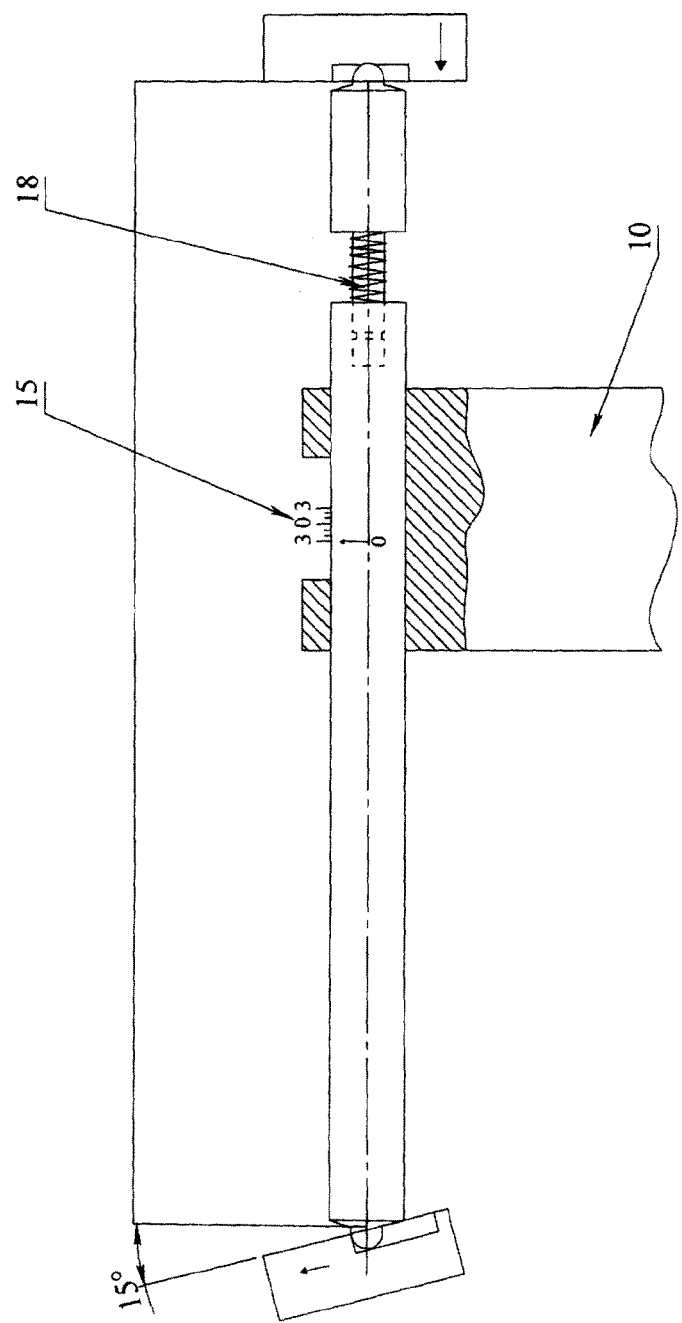
FIG. 4 presents a section of articulator's mechanical joint, with the following numbered details 10,15,18.
Figure 5:
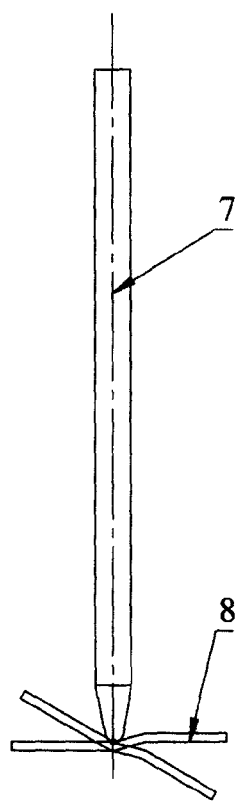
FIG. 5 is the drawing of the projection of incisive pin 7 and of the incisive platform 8.
Figure 7:
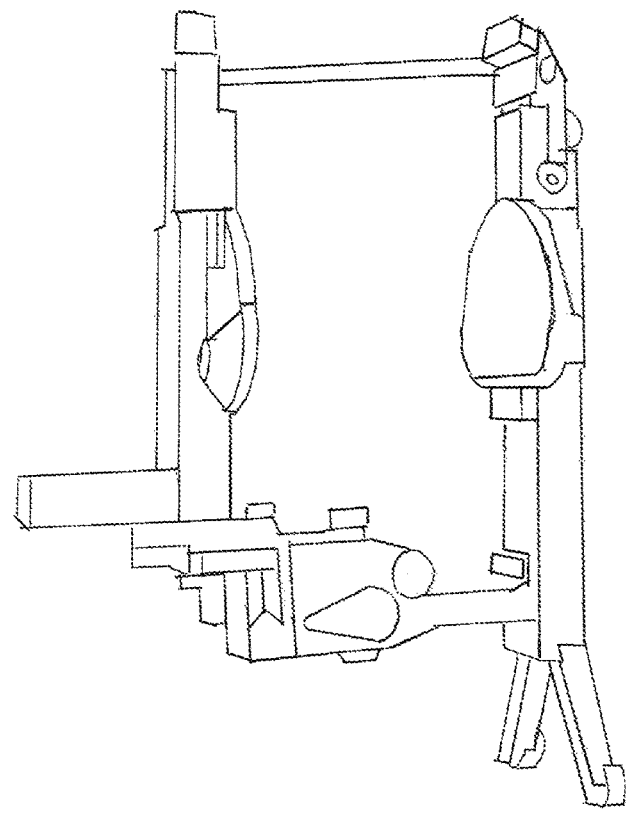
FIG. 7 is a lateral view of the articulator depicted in FIG. 1, with ascended elevator 4.
Figure 6:
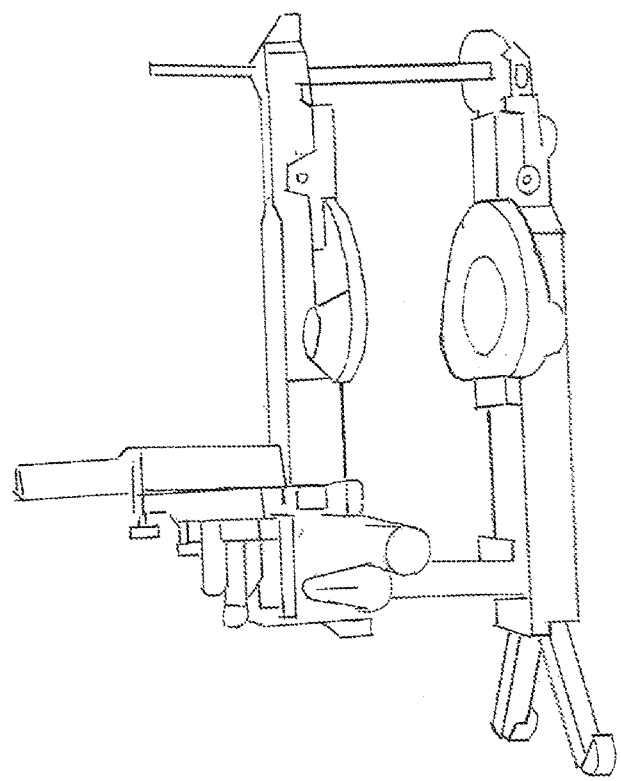
FIG. 6 presents a lateral view of the articulator depicted in FIG. 1, with descended elevator 4.

Description of the details designated at FIG. 1, 2, 3, 4, 5, 6, 7, 8: 1—base; 2—plank; 3—body of the joint cavity; 4—elevator; 5—upper horizontal shoulder; 6—lower working plate; 7—incisive pin; 8—incisive platform; 9—joint cavity carrier; 10—vertical body; 11—upper vertical body; 12—pawl; 13—elbow; 14—joint head axes; 15—scale of axis lateral shift; 16—scale for the inclination of the incisive platform; 17—scale for the inclination of the protrusion (sagittal) condyle path; 18—elastic element; 19—fixator; 20—special screw; 21—lower part; 22—upper part; 23—screw; 24—upper working plate.

Examples of Performance

A semi-adjustable, arcon-type articulator includes base 1, over which lower working plate 6 is located. At the front, incisive platform 8 is assembled on base 1. At the rear of base 1, base 1 is immovably connected to lower vertical body 10, to which horizontal axis is assembled with two joint heads 14. In the middle of the axis, at the rear of lower vertical body 10, scale 15 is outlined for reporting the axis lateral shift on the left and on the right and elastic element 18 is inbuilt. The axis with the two joint heads 14 is movably fixed, with the blocking capability, with the aid of fixator 19 to concave longitudinal groove, one on the left and one on the right that is located inside the body of joint cavity 3. In upper part 22 on the outside of both bodies of joint cavities 3, on the left and on the right pawl 12 and screw 23 are located with which to regulate scale 17 for the inclination of the protrusion (sagittal) condyle path, located at joint cavity carrier 9. Both bodies of joint cavities 3 are connected with plank 2 in the middle that in turn is immovably connected to upper vertical body 11, which at the front of upper vertical body 11 is connected to upper horizontal shoulder 5, under which magnetically connected upper working plate 24 is located. At the front of upper horizontal shoulder 5, incisive pin 7 is assembled that leans at incisive platform 8.

Lower vertical body 10 and upper vertical body 11 at the rear could be immovably blocked and de-blocked via elbow 13. At the front of upper vertical body 11 elevator 4 is adapted Operating the Articulator—Semiadjustable, Arcon The lower mandible working model is fixed for example with gypsum and centered at lower working plate 6, which is magnetically connected to base 1 in a manner that results in the lower mandible working model's middle line and the articulator's middle line coinciding and the chewing plane of the model could be horizontally located at the work bench. The upper maxillar model is juxtaposed to the lower mandible working model in central position. Along the upper mandible working model minimum gypsum quantity and upper working plate 24 are placed, as the latter is magnetically connected to upper horizontal shoulder 5, which is immovably connected to elevator 4, fixed at the front of upper vertical body 11 and capable of moving up and down until propping up the upper working model and connecting to it. Lower vertical body 10 is immovably connected to base 1, and upper vertical body 11 is immovably connected on one hand to upper horizontal shoulder 5, and on the other hand to plank 2, which is immovably connected to carrier 9, to which the body of joint cavity 3 is connected, one on the left and one on the right. Lower vertical body 10 and upper vertical body 11 could be blocked and de-blocked via elbow 13 thus base 1 and upper horizontal shoulder 5 could remain in continuous inter-parallel location while operating the articulator. In the middle of the axis with the two joint heads 14, scale 15 is outlined at the rear for reporting the lateral shift on the left and on the right, and this extension and shortening movement could be performed by elastic element 18, inbuilt in the axis with the two joint heads 14, which are adapted to both bodies of the joint cavities 3 and via the fixator 19 they could be blocked in central position or perform opening and closing movement, in retrusion, laterotrusion and mediotrusion, with the reproduction of progressive and immediate lateral shift, as well as opportunity for detaching lower 21 from upper 22 part of the articulator and fixing them once again with pin 12. With screw 23 you could fix the inclination of the protrusion (sagittal) condyle path according to scale 17, which is located at the external side of carrier 9. Incisive platform 8, being propped up by incisive pin 7 is assembled at the front of base 1 and it could rotate, as its inclination could be blocked with special nut 16 and reported at scale 20.

The advantage of the semi-adjustable, arcon-type articulator is that the operations with it are facilitated, materials consumption is lowered, and the accuracy and precision of the prepared dental prostheses are improved.

The invention claimed is:

1. A semi-adjustable arcon-type articulator comprising:
a set of lower parts including: a base having a front and a rear, a lower working plate located over the base, an incisive platform assembled at the front of the base, a lower vertical body immovably connected to the rear of the base, a horizontal axis rod having a first joint head and a second joint head, wherein the horizontal axis rod is coupled to the lower vertical body between said first joint head and said second joint head;
a first joint cavity body coupled to the first joint head forming a first mechanical joint;
a second joint cavity body coupled to the second joint head, forming a second mechanical joint;
a set of upper parts including: a plank connecting the first joint cavity body and the second joint cavity body, an upper vertical body having a front, the plank immovably connected to the upper vertical body, an upper horizontal shoulder having a front and a rear, the rear of the upper horizontal shoulder connected to the front of the upper vertical body, an upper working plate magnetically connected under the upper horizontal shoulder, and an elevator coupled to the front of the upper vertical body, the elevator configured to move along the upper vertical body, the upper horizontal shoulder immovably connected to the elevator;
wherein the set of upper parts is detachably interconnected with and rotatable relative to the set of lower parts about the horizontal axis rod at said first and second mechanical joints respectively;
an incisive pin assembled at the front of the upper horizontal shoulder and extending to the incisive platform; and
an elbow configured to lock and unlock the upper vertical body with the lower vertical body, wherein said locking ensures continuous parallel orientation of the base and the upper horizontal shoulder while operating the articulator.

2. The semi-adjustable arcon-type articulator of claim 1, further comprising:
a scale located in a middle of the horizontal axis rod, the horizontal axis rod including an elastic element, wherein the elastic element enables the horizontal axis rod to be lengthened and shortened to produce intermediate lateral shift of the first and second mechanical joints, wherein any lengthening and/or shortening is measurable by the scale.

3. The semi-adjustable arcon-type articulator of claim 2, further comprising:
   a scale located in the front of the base and under the incisive platform; and a locking element; wherein the incisive platform is rotatably adjustable, wherein a rotatable adjustment is measurable by the scale; and wherein the locking element is configured to lock the incisive platform from said rotatable adjustment.

\* \* \* \* \*

UNITED STATES PATENT AND TRADEMARK OFFICE
CERTIFICATE OF CORRECTION

PATENT NO. : 9,888,986 B2  
APPLICATION NO. : 15/107731  
DATED : February 13, 2018  
INVENTOR(S) : Andon Dimitrov Filtchev Page 1 of 1

It is certified that error appears in the above-identified patent and that said Letters Patent is hereby corrected as shown below:

In the Claims

Claim 3 (Column 5, Line 1): "The semi-adjustable arcon-type articulator of claim 2," should read "The semi-adjustable arcon-type articulator of claim 1,"

Signed and Sealed this  
Twenty-sixth Day of March, 2019

Andrei Iancu  
*Director of the United States Patent and Trademark Office*